(12) United States Patent
Langer et al.

(10) Patent No.: US 9,046,475 B2
(45) Date of Patent: Jun. 2, 2015

(54) HIGH ELECTRON ENERGY BASED OVERLAY ERROR MEASUREMENT METHODS AND SYSTEMS

(75) Inventors: Moshe Langer, Nes Ziona (IL); Ofer Adan, Rehovot (IL); Ram Peltinov, Tel Aviv (IL); Yoram Uziel, Post Misgav (IL); Ori Shoval, Ashdod (IL)

(73) Assignee: APPLIED MATERIALS ISRAEL, LTD., Rehovot (IL)

(*) Notice: Subject to any disclaimer, the term of this patent is extended or adjusted under 35 U.S.C. 154(b) by 26 days.

(21) Appl. No.: 13/111,838

(22) Filed: May 19, 2011

(65) Prior Publication Data

US 2012/0292502 A1    Nov. 22, 2012

(51) Int. Cl.
*G21K 7/00* (2006.01)
*G01N 23/225* (2006.01)

(52) U.S. Cl.
CPC ........ *G01N 23/2251* (2013.01); *G01N 2223/61* (2013.01); *G01N 2223/611* (2013.01)

(58) Field of Classification Search
CPC ........ H01J 37/00; H01J 37/02; H01J 37/147; H01J 37/20; H01J 37/21; H01J 37/22; H01J 37/222
USPC ......... 250/306, 307, 311, 492.1, 491.1, 492.3
See application file for complete search history.

(56) References Cited

U.S. PATENT DOCUMENTS

| 3,849,659 A | 11/1974 | O'Keeffe |
| H589 H * | 2/1989 | Sartore ............ 250/307 |
| 4,896,036 A | 1/1990 | Rose et al. |
| 4,926,054 A | 5/1990 | Frosien |
| 5,659,172 A | 8/1997 | Wagner et al. |
| 5,866,905 A * | 2/1999 | Kakibayashi et al. ........ 250/311 |
| 5,895,917 A | 4/1999 | Ueda et al. |

(Continued)

FOREIGN PATENT DOCUMENTS

| JP | 2003-158163 A | 5/2003 |
| WO | 99/46797 A1 | 9/1999 |

(Continued)

OTHER PUBLICATIONS

Frosien, J. "Compound Magnetic and electrostatic Lenses for Low-Voltage Applications", Journal of Vacuum Science and Technology: Part B, American Institute of Physics, New York US, vol. 7, No. 6, 18XP000117179, ISSN: 1071-1023, Nov. 1, 1989), 1871-1877.

(Continued)

*Primary Examiner* — Nicole Ippolito
*Assistant Examiner* — Jason McCormack
(74) *Attorney, Agent, or Firm* — Kilpatrick Townsend & Stockton LLP

(57) ABSTRACT

A method, a system and a computer readable medium are provided. The method may include obtaining or receiving first area information representative of a first area of a first layer of an inspected object; wherein the inspected object further comprises a second layer that comprises a second area; wherein the second layer is buried under the first layer; directing electrons of a primary electron beam to interact with the first area; directing electrons of the primary electron beam to interact with the second area; generating detection signals responsive to electrons that were scattered or reflected from at least one of the first and second areas; and determining at least one spatial relationship between at least one feature of the first area and at least one feature of the second area based on the detection signals and on the first area information.

19 Claims, 11 Drawing Sheets

(56) References Cited

U.S. PATENT DOCUMENTS

| | | | |
|---|---|---|---|
| 5,900,629 | A | 5/1999 | Todokoro et al. |
| 5,939,720 | A | 8/1999 | Todokoro |
| 5,952,241 | A | 9/1999 | Baker et al. |
| 6,037,589 | A | 3/2000 | Yonezawa et al. |
| 6,064,486 | A | 5/2000 | Chen et al. |
| 6,066,853 | A | 5/2000 | Nakasuji |
| 6,172,365 | B1 | 1/2001 | Hiroi et al. |
| 6,184,526 | B1 | 2/2001 | Kohama et al. |
| 6,194,729 | B1 | 2/2001 | Weimer |
| 6,232,601 | B1 | 5/2001 | Schmitt et al. |
| 6,287,734 | B2 | 9/2001 | Imai |
| 6,291,870 | B1 | 9/2001 | Kawashima et al. |
| 6,365,897 | B1 | 4/2002 | Hamashima et al. |
| 6,407,388 | B1 | 6/2002 | Frosien |
| 6,407,396 | B1 | 6/2002 | Mih et al. |
| 6,463,184 | B1 | 10/2002 | Gould et al. |
| 6,489,068 | B1 | 12/2002 | Kye |
| 6,498,068 | B1 | 12/2002 | Ueda et al. |
| 6,501,077 | B1 | 12/2002 | Sawahata et al. |
| 6,555,819 | B1 | 4/2003 | Suzuki et al. |
| 6,589,385 | B2 | 7/2003 | Minami et al. |
| 6,590,210 | B1 | 7/2003 | Essers |
| 6,674,075 | B2 | 1/2004 | Petrov et al. |
| 6,778,275 | B2 | 8/2004 | Bowes |
| 6,787,773 | B1 * | 9/2004 | Lee .................. 250/311 |
| 6,897,442 | B2 | 5/2005 | Petrov |
| 7,279,258 | B2 * | 10/2007 | Goodwin .................. 430/30 |
| 7,842,933 | B2 * | 11/2010 | Shur et al. ............. 250/491.1 |
| 2002/0070340 | A1 * | 6/2002 | Veneklasen et al. ......... 250/310 |
| 2002/0149381 | A1 * | 10/2002 | Lo et al. .................. 324/751 |
| 2002/0185599 | A1 | 12/2002 | Kimura et al. |
| 2005/0089773 | A1 * | 4/2005 | Shur et al. .................. 430/22 |
| 2005/0184237 | A1 * | 8/2005 | Takane et al. .............. 250/311 |
| 2007/0221842 | A1 * | 9/2007 | Morokuma et al. .......... 250/307 |
| 2008/0149831 | A1 * | 6/2008 | Saito .......................... 250/310 |
| 2008/0270081 | A1 * | 10/2008 | Bearup et al. ............... 702/189 |
| 2009/0152463 | A1 * | 6/2009 | Toyoda et al. .............. 250/311 |
| 2011/0139982 | A1 * | 6/2011 | Kijima et al. ............... 250/307 |
| 2011/0266440 | A1 * | 11/2011 | Boughorbel et al. ......... 250/310 |

FOREIGN PATENT DOCUMENTS

| | | |
|---|---|---|
| WO | 01/45136 A1 | 6/2001 |
| WO | 02/37523 A2 | 5/2002 |
| WO | WO 2010038368 A1 * | 4/2010 |

OTHER PUBLICATIONS

Applied Materials Israel, Ltd., International Search Report and Written Opinion, PCT/US2004/012468 filed Apr. 22, 2004, ISA/EP, mailed Oct. 29, 2004, 15 pp.

Applied Materials, Inc.; PCT/US03/15018 filed May 12, 2003; International Search Report, ISA/EP, mailed Jan. 26, 2004, 8 pp.

Patent Abstracts of Japan, vol. 1998, No. 13, Nov. 30, 1998—& JP 10 214586 A (Horon: KK), Aug. 11, 1998, abstract; figures 1, 2.

Patent Abstracts of Japan, vol. 1999, No. 11, Sep. 30, 1999, JP 11 162384 1 pg.

Patent Abstracts of Japan, vol. 01, No. 385 (P-1094), Aug. 20, 1990—& JP 02 145947 A (Shimadzu Corp), Jun. 5, 1990, abstract; figure 1.

English Translation and Office Action for Japanese Application No. 2011-159378 mailed Jul. 31, 2013, 4 pages.

* cited by examiner

HIGH ELECTRON ENERGY BASED OVERLAY ERROR MEASUREMENT METHODS AND SYSTEMS

BACKGROUND OF THE INVENTION

Overlay Error Measurements

Integrated circuits are very complex devices that include multiple layers. Each layer may include conductive material, isolating material while other layers may include semi-conductive materials. These various materials are arranged in patterns, usually in accordance with the expected functionality of the integrated circuit. The patterns also reflect the manufacturing process of the integrated circuits.

Each layer is formed by a sequence of steps that usually includes depositing a resistive material on a substrate/layer, exposing the resistive material by a photolithographic process, and developing the exposed resistive material to produce a pattern that defines some areas to be later etched.

Ideally, each layer is perfectly aligned to a previously existing layer. Typically, the layers are misaligned, thus a misalignment or overlay error exists between each pair of layers.

Various techniques evolved for observing overlay errors, some using optical instruments and some using scanning electron microscopes. U.S. Pat. No. 6,407,396 of Mih et al., U.S. Pat. No. 6,489,068 of Kye, U.S. Pat. No. 6,463,184 of Gould et al., U.S. Pat. No. 6,589,385 of Minami et al and U.S. Pat. No. 7,842,933 of Shur et al., all being incorporated herein by reference, provide a good indication about the state of art overlay error measurement techniques.

Optical overlay measurements are subjected to various errors such as lens aberrations of the optical system. Mih states that in some cases Atomic Force Microscopy or Scanning Electron Microscopy metrology techniques may be necessary to verify the optical overlay measurement accuracy.

Double patterning is a class of patterning techniques designed to increase the density of circuit features that can be produced on the wafer beyond what the normal limits of a particular lithography scanner. Double patterning can include manufacturing an inspected object that has a first layer and a second layer. The second layer is buried under the first layer. Each layer having features (patterns) that are very close to each other. These features may be eventually etched during the double patterning process.

It is noted that detecting overlay errors after the top layer is etched can be very costly.

Interaction Between Charged Electron Beam and an Inspected Object

Once an electron beam hits an inspected object various interaction processes occur. A detailed description of these processes can be found at "Scanning electron microscopy". L. Reimer, second edition, 1998, which is incorporated herein by reference.

FIG. 1 illustrates the important interaction processes and various information volumes. An information volume is a space in which interaction processes occur and result in scattering or reflection of electrons that may be eventually detected to provide information about the information volume.

The figure illustrates a primary electron beam 2 that hits an inspected object 9. As a result, secondary electrons 2 and Auger electrons 4 are emitted from a very thin information volume 3 while back scattered electrons (BSE) 6 and X-ray electrons 8 can leave the inspected object from a relatively large information volume 5 that has a depth that may even exceed one micron.

Secondary electrons are easy to detect as their trajectory can be relatively easily changed such that they are directed toward a detector. The trajectory of backscattered electrons is relatively straight and is slightly affected by electrostatic fields.

FIG. 2 illustrates a first type of a prior art multi-perspective SEM 10 that includes multiple detectors. SEM 10 includes an electron gun (not shown) for generating a primary electron beam, as well as multiple control and voltage supply units (not shown), an objective lens 12, in-lens detector 14 and external detectors 16. System 10 also includes deflection coils and a processor (not shown). Such a system is described at U.S. Pat. No. 5,659,172 of Wagner.

In system 10 the primary electron beam is directed through an aperture 18 within the in-lens detector 14 to be focused by the objective lens 12 onto an inspected wafer 20. The primary electron beam interacts with wafer 20 and as a result various types of electrons, such as secondary electrons, back-scattered electrons, Auger electrons and X-ray quanta are reflected or scattered. Secondary electrons can be collected easily and most SEMs mainly detect these secondary electrons.

System 10 is capable of detecting some of the emitted secondary electrons by in-lens detector 14 and by external detectors 16.

Objective lens 12 includes an electrostatic lens and a magnetic lens that introduce an electrostatic field and a magnetic field that leak from the lens towards the wafer. The collection of secondary electrons is highly responsive to the leaked electrostatic field, while it is hardly influenced by the leaked magnetic field.

The leaked electrostatic field attracts low energy secondary electrons and very low energy secondary electrons into the column. A significant part of the very low enemy secondary electrons are directed through the aperture of in-lens detector 14 and are not detected. Low energy secondary electrons are directed towards the in-lens detector 14. High-energy secondary electrons are detected if their initial trajectory is aimed towards one of the detectors.

An effective defect review tool requires both types of detectors in order to capture all types of defects. In-lens detector 14 is usually used for determining a contrast between different materials, and is also useful in voltage contrast mode as well as in HAR mode. HAR mode is used to inspect cavities that are characterized by a High Aspect Ratio (in other words—cavities that are narrow and deep). During HAR mode, the area that surrounds the cavity is usually charged to allow electrons from the lower portion of the cavity to reach the detector. The in-lens detector 14 is also very sensitive to pattern edges. External detectors 16 are much more sensitive to the topography of the wafer. The external detectors are also less susceptible to wafer charging, which is significant when imaging highly resistive layers.

U.S. Pat. No. 6,555,819 of Suzuki et al. (which is incorporated herein by reference) describes a multi-detector SEM having magnetic leakage type objective lens where the magnetic field largely influences the trajectory of emitted secondary electrons. This SEM has various disadvantages, such as not being capable of providing tilted images and is not efficient to provide images from holes of high aspect ratio. Suzuki has a reflector that includes an aperture through which the primary electron beam passes, thus reflected electrons may pass through this aperture and remain un-detected.

There is a need to provide an efficient system and method that facilitate overlay measurements.

SUMMARY OF THE INVENTION

According to an embodiment of the invention a method for evaluating overlay may be provided. The method may include obtaining or receiving first area information representative of a first area of a first layer of an inspected object; wherein the inspected object further comprises a second area that comprises a second area; wherein the second layer is buried under the first layer; directing electrons of a primary electron beam to interact with the first area; directing electrons of the primary electron beam to interact with the second area; generating detection signals responsive to electrons that were scattered or reflected from at least one of the first and second areas; and determining at least one spatial relationship between at least one feature of the first area and at least one feature of the second area based on the detection signals and on the first area information.

The method may include obtaining first area information by directing electrons of the primary electron beam to interact with the first area without substantially interacting with the second area; and generating detection signals responsive to electrons that were scattered or reflected from the first area.

The method may include generating detection signals that are responsive to secondary electrons that were scattered or reflected from the first area while ignoring backscattered electrons that were scattered from the inspected object.

According to an embodiment of the invention a method for evaluating overlay can be provided and may include directing electrons of a primary electron beam to interact with a first area of a first layer of an inspected object; wherein the inspected object further may include a second layer that may include a second area; wherein the second layer is buried under the first layer; directing high landing energy electrons of the primary electron beam to interact with the second area; generating detection signals responsive to electrons that were scattered or reflected from at least one of the first and second areas; and determining at least one spatial relationship between at least one feature of the first area and at least one feature of the second area based on the detection signals, wherein an expected distance between a feature of the first area and a closest feature of the second layer is smaller than a pitch between adjacent features of the first area.

The method may include generating first area detection signal responsive to secondary electrons that were scattered or reflected from the first area; and generating second area detection signal responsive to backscattered electrons that were scattered or reflected from the second area.

The method may include receiving scattered light optics based overlay measurements and evaluating the overlay based on the detection signals and the scattered light based overlay measurements.

The method may include sending overlap information about the at least one spatial relationship to a scatterometry based overlay apparatus.

The method may include sending overlap information about the at least one spatial relationship to a diffraction based overlay apparatus.

According to an embodiment of the invention a system may be provided and may include a processor arranged to obtain or receive first area information representative of a first area of a first layer of an inspected object; wherein the inspected object further may include a second layer that may include a second area; wherein the second layer is buried under the first layer; electron optics arranged to direct electrons of a primary electron beam to interact with the first area and to direct electrons of the primary electron beam to interact with the second area; at least one detector arranged to generate detection signals responsive to electrons that were scattered or reflected from at least one of the first and second areas; and wherein the processor is further arranged to determine at least one spatial relationship between at least one feature of the first area and at least one feature of the second area based on the detection signals and on the first area information.

The electron optics may be arranged to direct electrons of the primary electron beam to interact with the first area without substantially interacting with the second area; wherein the at least one detector may be arranged to generate detection signals responsive to electrons that were scattered or reflected from the first area; and wherein the processor may be arranged to obtain the first area information by processing the detection signals.

The at least one detector may be arranged to generate detection signals that are responsive to secondary electrons that were scattered or reflected from the first area while ignoring backscattered electrons that were scattered from the inspected object.

According to an embodiment of the invention a system is provided and it may include: electron optics, arranged to: direct electrons of a primary electron beam to interact with a first area of a first layer of an inspected object; wherein the inspected object further may include a second layer that may include a second area; wherein the second layer is buried under the first layer; and direct high landing energy electrons of the primary electron beam to interact with the second area; at least one detector arranged to generate detection signals responsive to electrons that were scattered or reflected from at least one of the first and second areas; and a processor that may be arranged to determine at least one spatial relationship between at least one feature of the first area and at least one feature of the second area based on the detection signals, wherein an expected distance between a feature of the first area and a closest feature of the second layer is smaller than a pitch between adjacent features of the first area.

The at least one detector may include a secondary electron detector and a backscattered electron detector; wherein the secondary electron detector may be arranged to generate first area detection signal responsive to secondary electrons that were scattered or reflected from the first area; and wherein the backscattered electron detector may be arranged to generate second area detection signal responsive to backscattered electrons that were scattered or reflected from the second area.

The processor may be arranged to receive scattered light optics based overlay measurements and to evaluate the overlay based on the detection signals and the scattered light based overlay measurements.

The processor may be arranged to send overlap information about the at least one spatial relationship to a scatterometry based overlay apparatus.

The processor may be arranged to send overlap information about the at least one spatial relationship to a diffraction based overlay apparatus.

In any of the mentioned above methods or systems the primary electron beam may have a landing energy of at least 2000 electron volts, between 2000 and 5000 volts or even above 5000 electron volts.

According to an embodiment of the invention a computer program product is provided and may include a non-transitory computer readable medium that stores instructions for receiving first area information representative of a first area of a first layer of an inspected object; wherein the inspected object further comprises a second layer that comprises a second area; wherein the second layer is buried under the first layer; receiving detections signals detection signals responsive to electrons that were scattered or reflected from the first and from a second area of a second layer that is buried under the First layer; and determining at least one spatial relationship between at least one feature of the first area and at least one feature of the second area based on the detection signals and on the first area information. The non-transitory computer readable medium may store instructions for executing any method described in the specification.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

Figure 1:
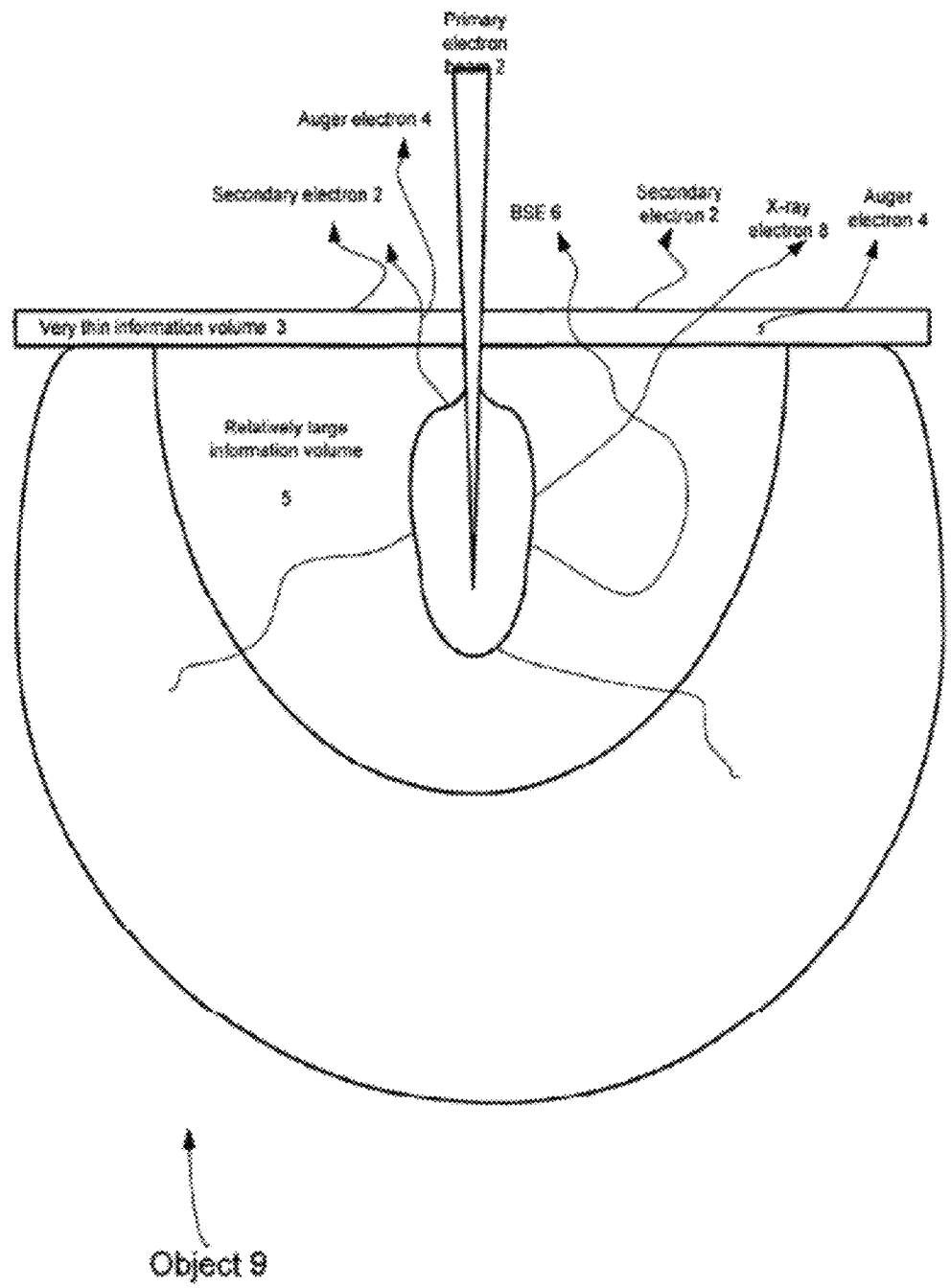
FIG. 1 illustrates various interaction processes and their respective information volumes.
Figure 2:
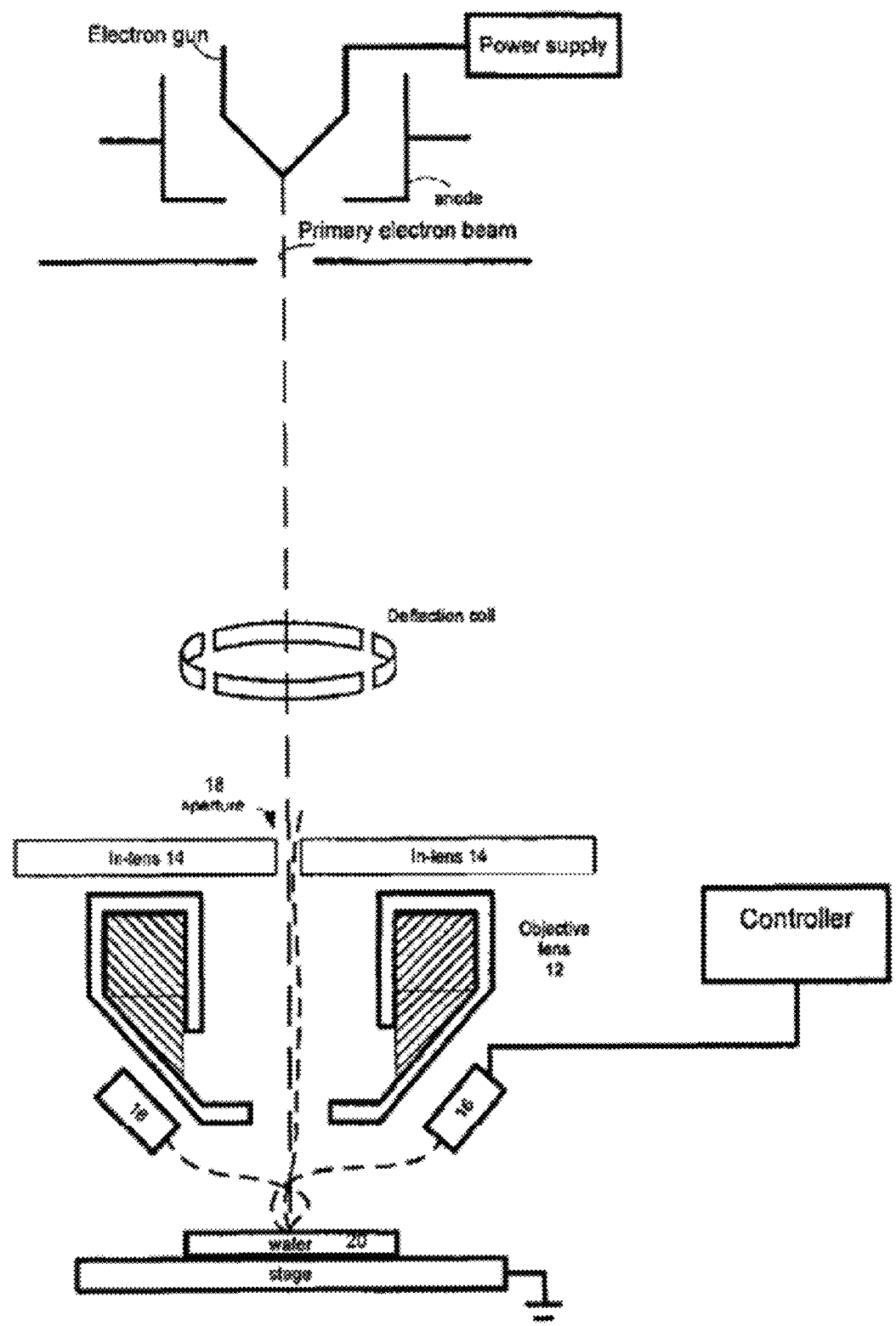
FIG. 2 describes a portion of a multi-detector Scanning Electron Microscope (SEM)

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In all figures the same reference numbers represent the same elements.

According to various embodiments of the invention, methods and systems for evaluating overlay errors are provided and include illuminating an inspected object with a primary electron beam that has electrons that have enough energy to interact with one or more buried layers. Secondary electrons and, additionally or alternatively, backscattered electrons are detected by in-lens and inner-lens detectors to provide detection signals. The detection signals are processed to provide an indication about the shape and location of features of a top layer (first layer) and a buried layer (second layer) of an inspected object. It is noted that the terms first and second are merely used to differentiate one element from another.

The various methods can be applied on a variety of inspected objects including but not limited to ultra thin double patterning manufactured objects. It is noted that in lithography applications the top layer is typically made of photoresist and the buried layer is typically made of an etched material, usually a nitride used for a hard mask immersed in BARC. In directed self assembly the top and buried layers are made of a hydrophilic and hydrophobic block co polymers that climb one on top of the other during the self assembly process. The methods and systems described in this specification can be applied to such layers or to other layers.

The imaging of deeper (wider) layers (or less transparent) may result in lower signal to noise ratio (SNR) images. In this case further processing may be required in order to reconstruct these lower SNR images. Any known image cleaning, edge detection or other low SNR image processing methods may be applied on such images.

Figure 3:
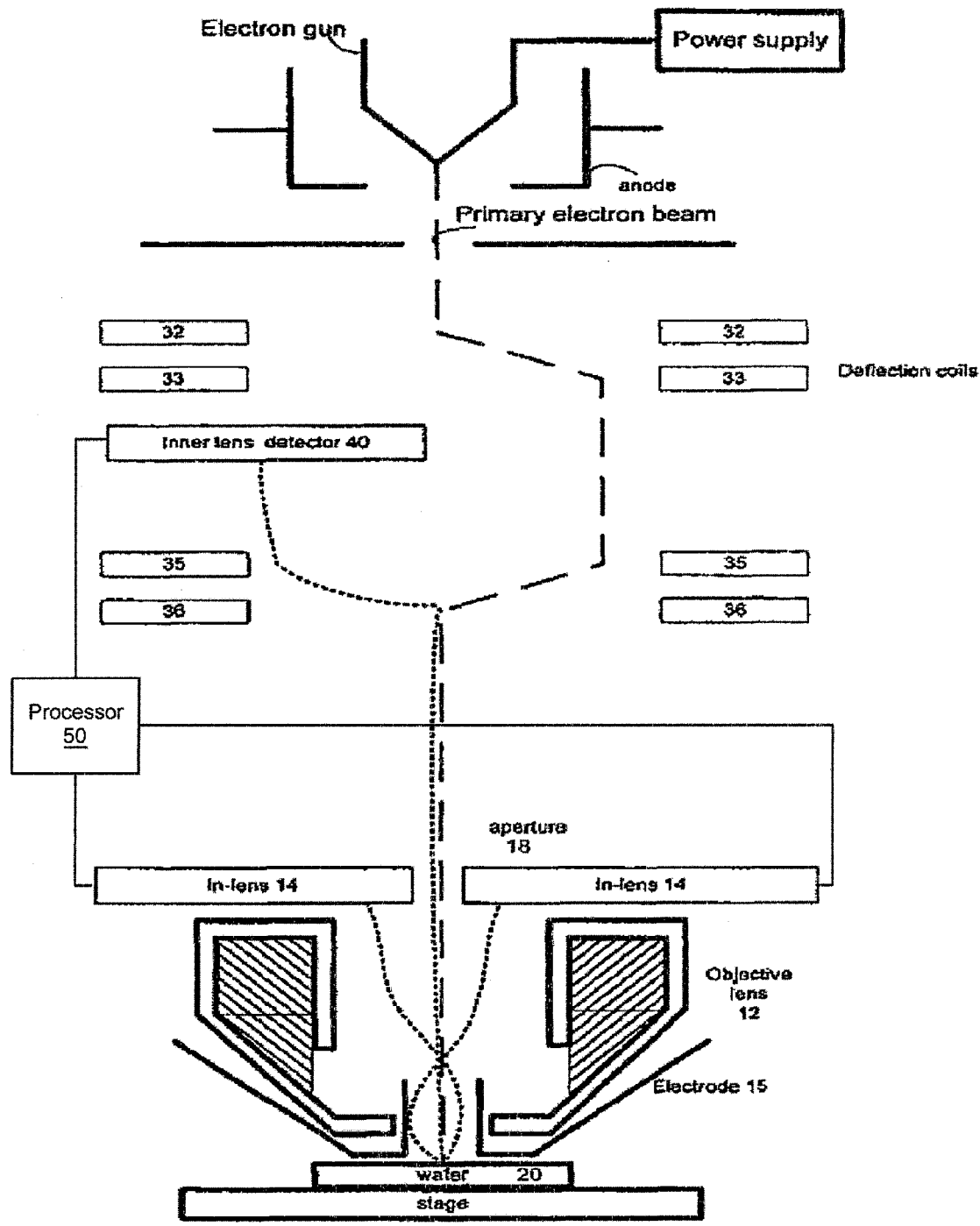
FIG. 3 illustrates a portion of another multi-detector SEM.

FIG. 3 is an illustration of a portion 10' of another multiple-detector SEM. An example of such a system is provided in U.S. Pat. No. 7,842,933 which is incorporated herein by reference.

FIG. 3 also illustrates an exemplary path of a primary electron beam, as well as the paths of electrons that are scattered or reflected from an inspected object, such as but not limited to a wafer or a reticle.

The primary electron beam propagates along an optical axis and is then (i) tilted in a first direction, (ii) tilted in an opposite direction such as to propagate along a secondary optical axis that is parallel to the optical axis but spaced apart from the optical axis, (iii) tilted, in a second direction, towards the optical axis and then (iv) tilted, in a direction opposing the second direction, such as to propagate along the optical axis. The above-mentioned tilt operations may be generated by magnetic deflection coils 32-36. A system and method for double tilt is described in U.S. patent application Ser. No. 10/146,218 filed 13 May 2002, and is incorporated herein by reference. The electron beams are subjected to an electrostatic field that can be introduced by multiple electrodes of various shapes and arrangements. Some of the embodiments are illustrated in U.S. patent application Ser. No. 10/423,289 titled "objective lens arrangement for use in a charged particle beam column", incorporated herein by reference.

It is noted that other tilt schemes may be implemented, such as performing only the first two tilts, such that the primary electron beam interacts with the inspected object while propagating along the secondary axis.

In system 10' the primary electron beam is directed through an aperture 18 within the in-lens detector 14 to be focused by the objective lens 12 onto an inspected wafer 20. Secondary electrons that propagate through the aperture of in-lens detector 14 are eventually tilted in a second direction towards an inner-lens detector 40.

The in-lens detector is located at the final part of the propagation path, where the primary electron beam propagates along the optical axis. The in-lens detector has an aperture that is positioned such as to surround the optical axis.

Once electrons are emitted/scattered as a result of an interaction between the primary beam and the inspected object they are attracted, due to a strong electromagnetic field, towards the in-lens detector and to the aperture of that detector. The strength of the electrostatic field determines which secondary electrons are attracted to the in-lens detector and which are attracted to the aperture of the in-lens detector.

Secondary electrons that propagate through the aperture of in-lens detector 14 are eventually tilted in a second direction towards an inner-lens detector 40.

By applying a relatively strong electrostatic field the inner lens detector detects electrons that were once either not detected (passed through the aperture) or detected by the in-lens detector, while the in-lens detector detects electrons that once were detected by the external detectors.

Figure 4:
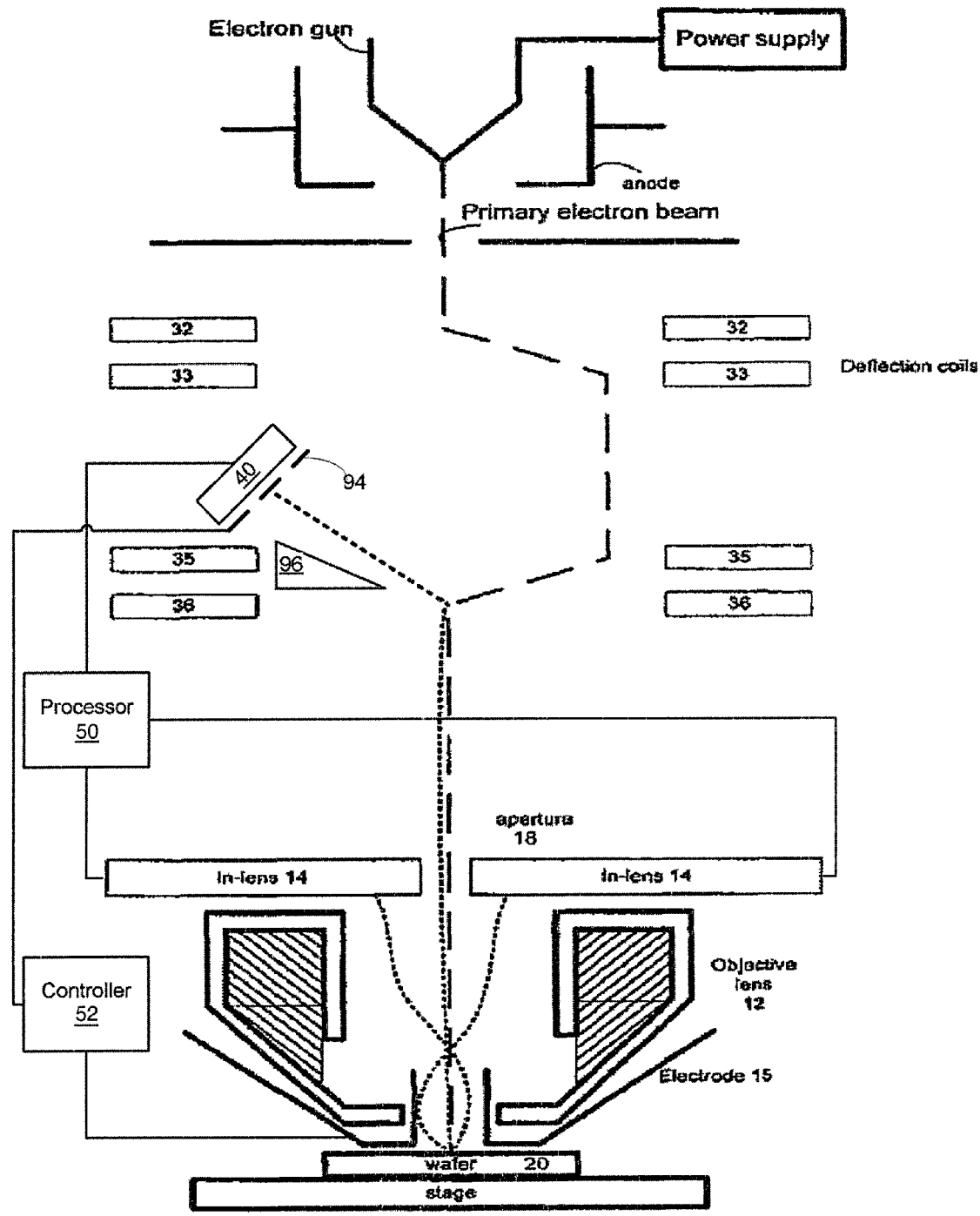
FIG. 4 illustrates a portion of another multi-detector SEM according to an embodiment of the invention.

FIG. 4 is an illustration of a portion 10" of a multiple-detector SEM according to an embodiment of the invention. FIG. 4 also illustrates an exemplary path of a primary electron beam, as well as the paths of electrons that are scattered or reflected from an inspected object, such as but not limited to a wafer or a reticle.

The primary electron beam propagates along an optical axis and is then (i) tilted in a first direction, (ii) tilted in an opposite direction such as to propagate along a secondary optical axis that is parallel to the optical axis but spaced apart from the optical axis, (iii) tilted, in a second direction, towards the optical axis and then (iv) tilted, in a direction opposing the second direction, such as to propagate along the optical axis.

The scattered electrons may be detected by the in-lens detector 14 or pass through the aperture 18 of the in-lens detector 14 and be deflected towards the inner-lens detector at a direction that may be oriented in relation to the optical axis. Additional deflecting element 96 is positioned near a portion of deflector 35 and prevents the system from performing yet a further deflection of the scattered electrons that pass through aperture 18. At an absence of deflecting element 96 an additional deflection occurs and the electrons may propagate towards the inner-lens detector 40 at a path that is parallel but spaced apart from the optical axis (as illustrated in FIG. 3).

FIG. 4 also shows the inner-lens detector 40 as being oriented in relation to the optical axis. The inner-lens detector 40 may be approximately normal to the trajectory of electrons that propagate towards the inner-lens detector 40. The inner-lens detector 40 can be preceded by a filter 94 that may prevent certain electrons from reaching the inner-lens detector 40—based on the landing energy of these electrons and a voltage potential applied to the filter 94. Different voltage potentials reject electrons having different landing energy. The filter can be used, for example, for allowing backscattered electrons while rejecting secondary electrons.

The inner-lens detector 40 and the in-lens detector 14 generate detection signals that are provided to processor 50. These detection signals can be processed to provide a single representation of the scanned areas (for example—a single image) or provide separate representations—the detection signals of each detector are processed independently.

Controller 52 can control the electrical potential of the grid 94, and additionally or alternatively of the objective lens—such as to control the detected by the detectors 14 and 40.

It is noted that when imaging only the first layer of an inspected object both detectors (14 and 40) can be set to detect the same type of electrons while when imaging both layers each detector can be used for detecting different types of electrons.

Figure 5:
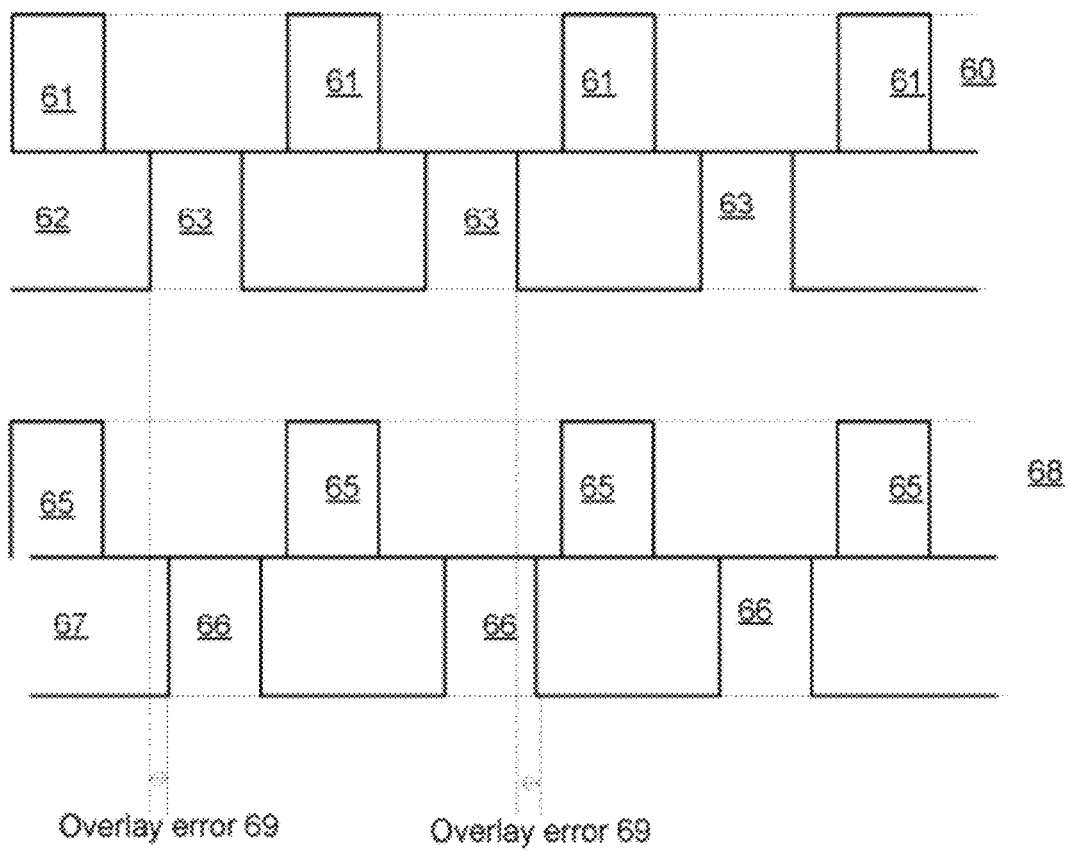
FIG. 5 illustrates an example of an overlay error.

FIG. 5 illustrates overlay errors 69 of a portion of an inspected object that is manufactured by the double patterning process. These overlay errors 69 are illustrated as a deviation of the actual features from desired features.

The upper part of FIG. 5 illustrates: (i) the location and shape of desired features 61 of a first layer 60, and (ii) the location and shape of desired features 63 of a second layer 62 buried underneath the first layer 60.

The lower part of FIG. 5 illustrates: (i) the location and shape of actual features 65 of a first layer 68, and (ii) the location and shape of actual features 66 of a second layer 67 that is buried underneath the first layer 68. The overlay errors 69 indicate that the actual features 66 of the second layer 67 are shifted to the right in relation to their desired locations.

FIG. 5 only illustrates an example of an overlay error. For example, different features of the same layer can differ from each other by their overlay errors, and additionally or alternatively, the overlay errors can include rotation.

Figure 7:
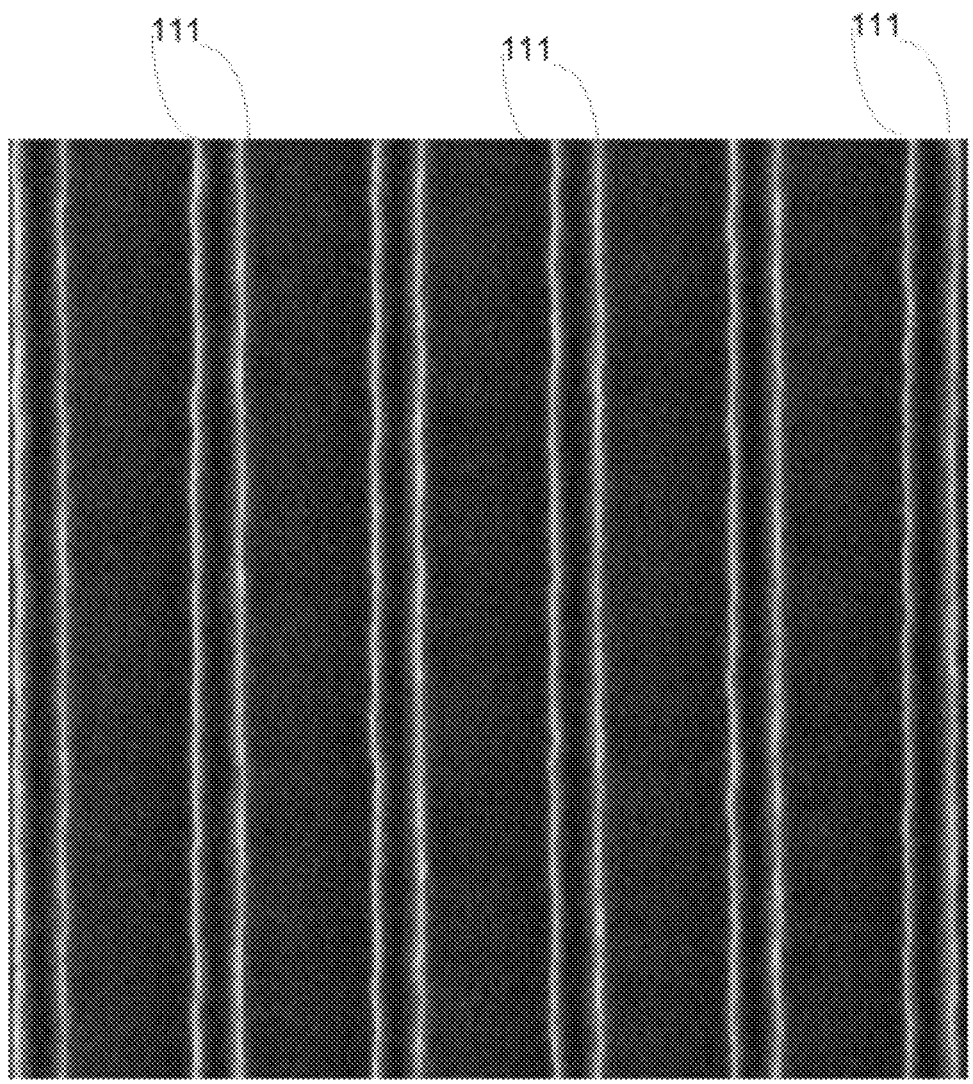
FIG. 7 is an image of a first area according to an embodiment of the invention.
Figure 8:
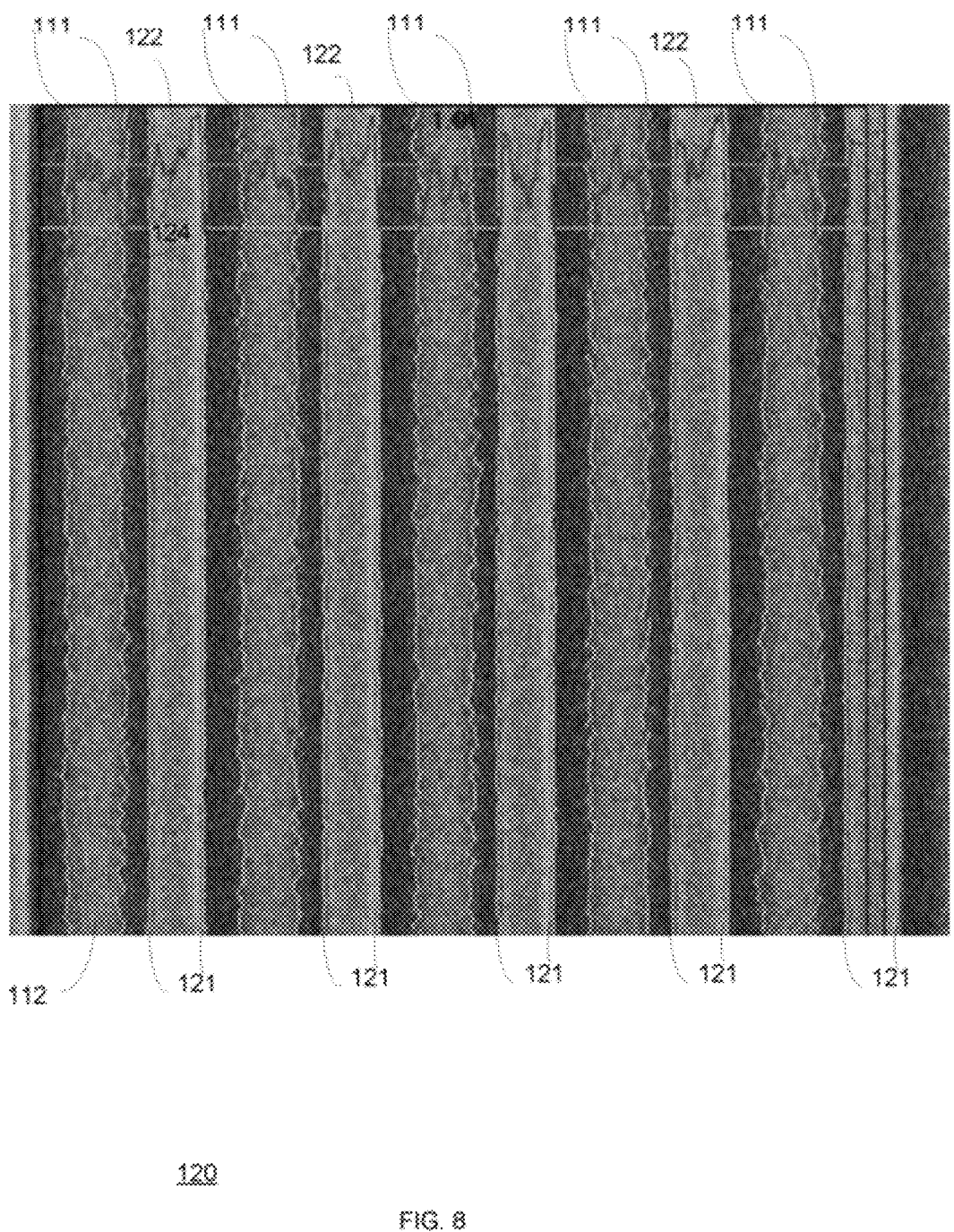
FIG. 8 is an image of a first area and of a second area buried under the first area, according to an embodiment of the invention.

FIG. 7 is an example of an image 110 of a first area of a first layer according to an embodiment of the invention and FIG. 8 is an example of an image 120 of the first area and of a second area of a second layer according to an embodiment of the invention.

FIG. 7 illustrates an image 110 of a first area and includes edges 111 that represent the locations of the features of a first layer. FIG. 8 is an image of the first area and of the second area and shows edges 111 of the features of the first area and edges 121 of features of the second area. These first and second area features may be perturbations and their upper portions 112 (for first area perturbations) and 122 (for second area perturbations) are illustrated as being brighter than their surroundings.

FIG. 8 also illustrates an intensity signal 124 indicative of an intensity of detection signals along an imaginary Y-axis (the features are substantially parallel to the X-axis). This intensity signal 124 provides an indication about the height of the different features of the first and second layers.

Figure 9:
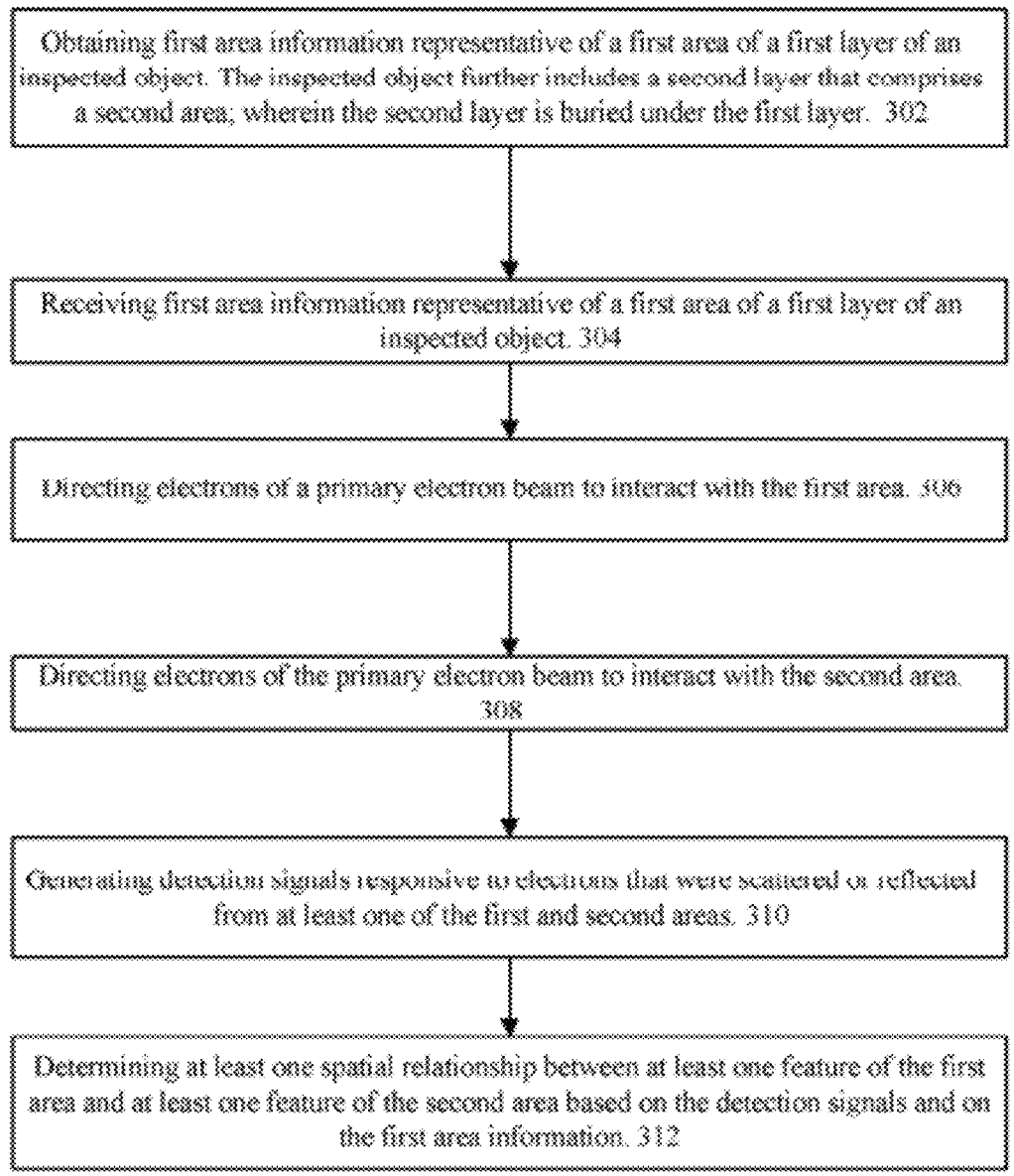
FIGS. 9-11 are flow charts illustrating methods for measuring overlay errors, according to various embodiments of the invention.

FIG. 9 illustrates a method 300 according to an embodiment of the invention.

Method 300 may start by either one of stages 302 and 304. It is noted that method 300 can include both stages 302 and 304 or only one of these stages.

Stage 302 includes obtaining first area information representative of a first area of a first layer of an inspected object. The inspected object further includes a second layer that comprises a second area wherein the second layer is buried under the first layer.

Stage 302 may include at least one of the following:
a. Obtaining first area information by directing electrons of the primary electron beam to interact with the first area without substantially interacting with the second area; and generating detection signals responsive to electrons that were scattered or reflected from the first area.
b. Generating detection signals that are responsive to secondary electrons that were scattered or reflected from the first area while ignoring backscattered electrons that were scattered from the inspected object.

Stage 304 includes receiving first area information representative of a first area of a first layer of an inspected object.

Stages 302 and 304 are followed by stage 306 of directing electrons of a primary electron beam to interact with the first area and by stage 308 of directing electrons of the primary electron beam to interact with the second area.

Stage 308 may include directing the primary electron beam towards the inspected object so that the electrons of the primary electron beam have a landing energy of at least 2000 electron volts or of at least 5000 electron volts.

Stages 306 and 308 are followed by stage 310 of generating detection signals responsive to electrons that were scattered or reflected from at least one of the first and second areas.

Stage 310 is followed by stage 312 of determining at least one spatial relationship between at least one feature of the first area and at least one feature of the second area based on the detection signals and on the first area information.

Stage 312 may include edge detection of edges of the at least one feature of the first area and of edges of the at least one feature of the second area.

Additionally or alternatively, stage 312 may include determination of the spatial relationship based on the edge detection and on the first area information. For example, a pair of a first area feature and a second area feature can partially overlap or have edges that overlap. In both cases the image can be substantially the same. The first area information can assist in differentiating between these two scenarios.

Figure 6:
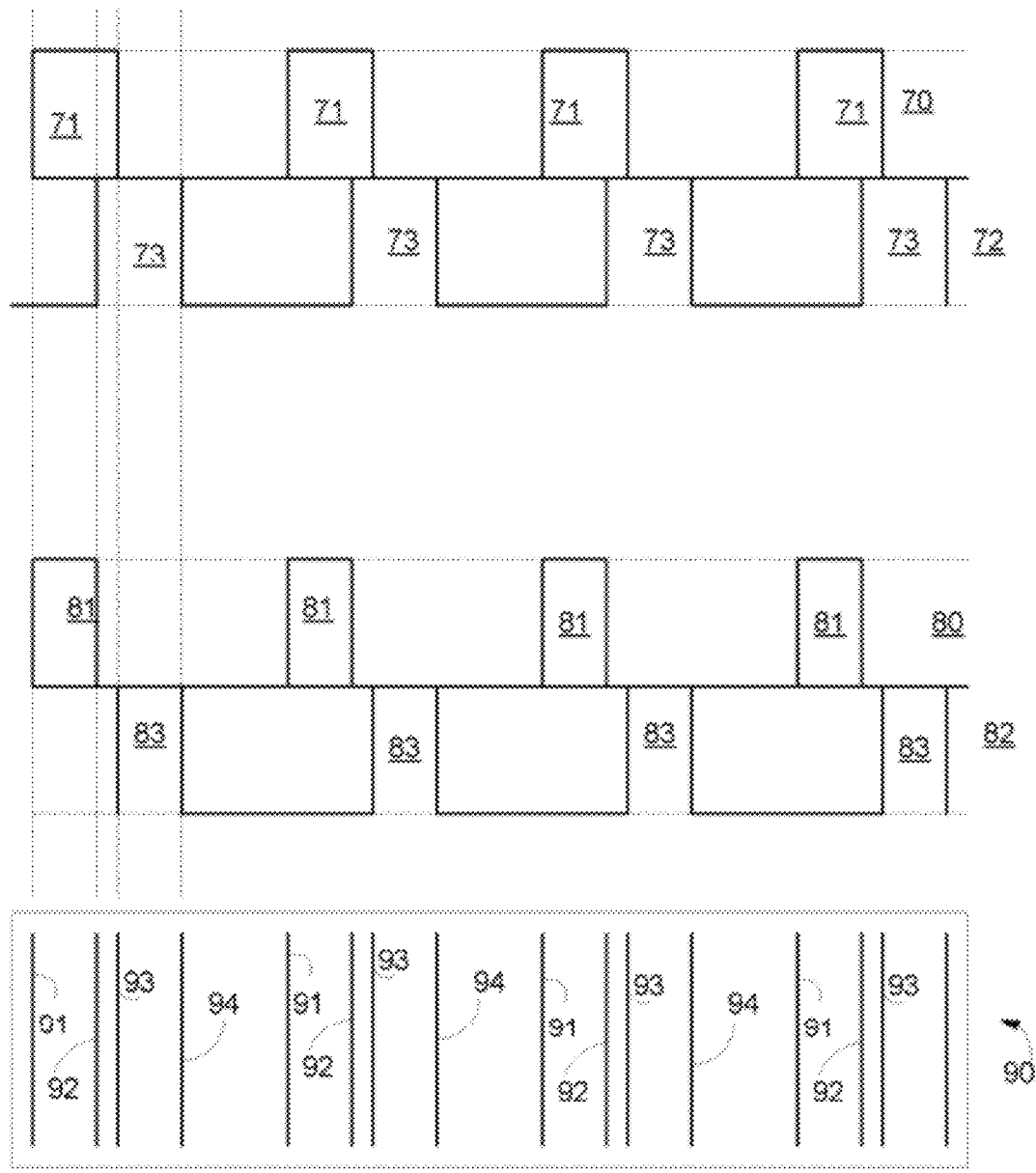
FIG. 6 illustrates two different portions of an inspected object and an edge image representative of the different portions, according to an embodiment of the invention.

This is illustrated in FIG. 6—the same edge image 90 with the same edges 91-94 can be obtained while imaging different objects (or different areas). The upper part of FIG. 6 illustrates over-lapping features (71 and 73) of different layers (70 and 72) while the middle part of FIG. 6 illustrates narrower features (81 and 83) that do not overlap. First area information such as the width of the features of the first and/or second layer can assist in differentiating between these scenarios.

Figure 10:
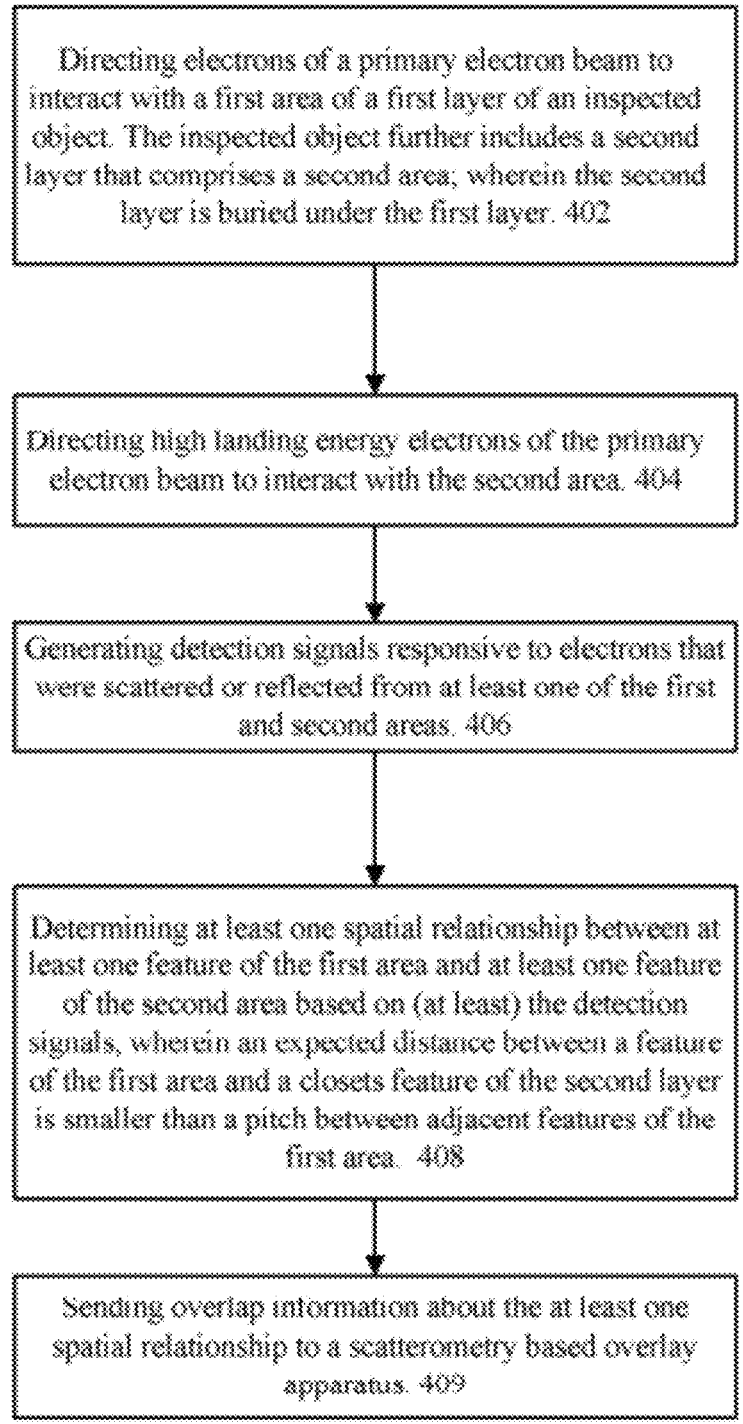

FIG. 10 illustrates a method 400 according to an embodiment of the invention.

Method 400 may start by stage 402 of directing electrons of a primary electron beam to interact with a first area of a first layer of an inspected object. The inspected object further includes a second layer that comprises a second area; wherein the second layer is buried under the first layer.

Stage 402 is followed by stage 404 of directing high landing energy electrons of the primary electron beam to interact with the second area.

Stage 404 is followed by stage 406 of generating detection signals responsive to electrons that were scattered or reflected from at least one of the first and second areas.

Stage 406 is followed by stage 408 of determining at least one spatial relationship between at least one feature of the first area and at least one feature of the second area based on (at least) the detection signals, wherein an expected distance between a feature of the first area and a closest feature of the second layer is smaller than a pitch between adjacent features of the first area. Thus, the first and second layers can be manufactured by a double patterning process or any other multiple patterning process.

According to an embodiment of the invention stage 408 may be followed by stage 409 of sending overlap information about the at least one spatial relationship to a scatterometry based overlay apparatus. This apparatus may use this information to determine the topography of the first layer.

Stage 406 may include generating first area detection signal responsive to secondary electrons that were scattered or reflected from the first area and generating second area detection signal responsive to backscattered electrons that were scattered or reflected from the second area.

Figure 11:
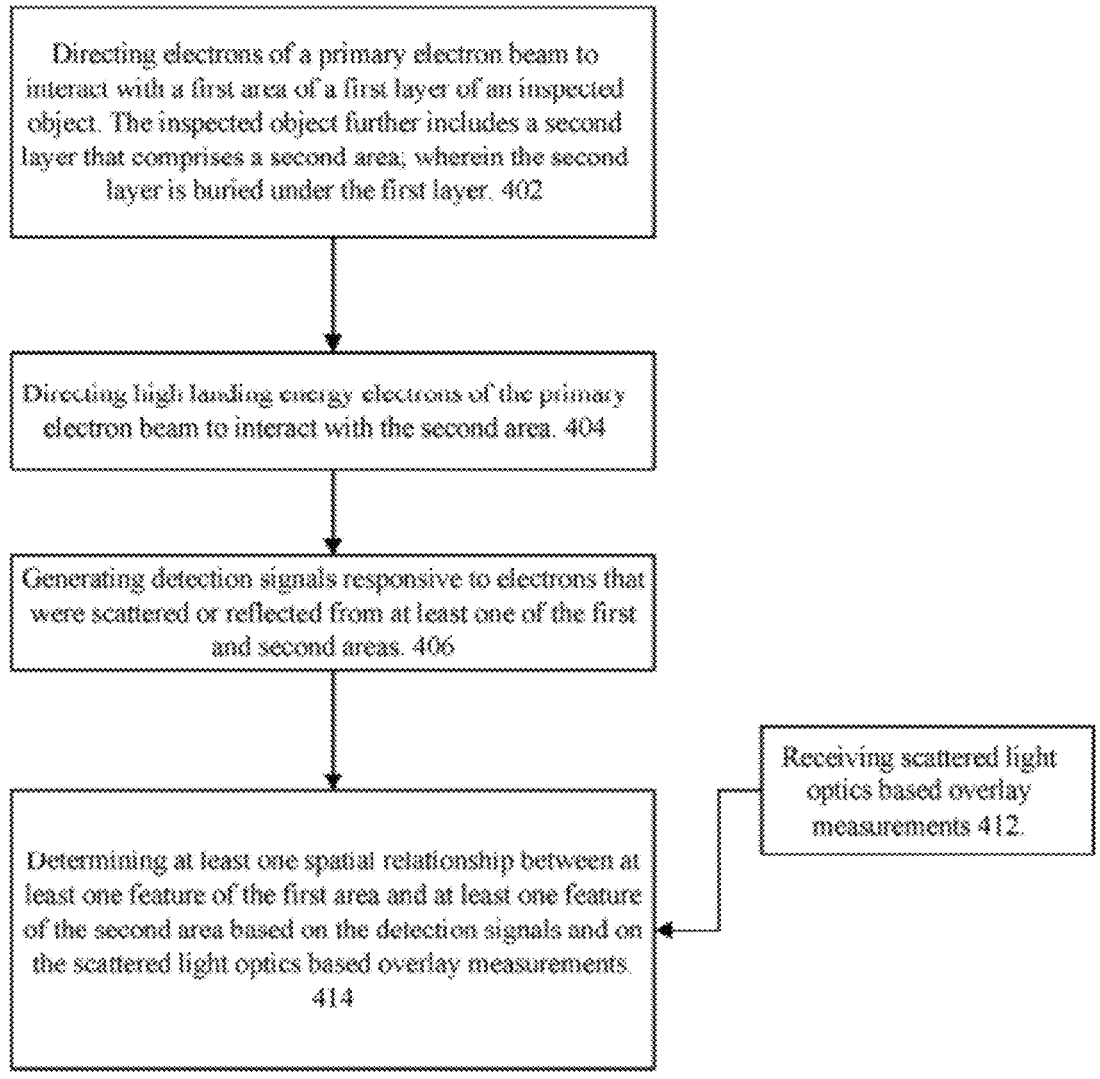

FIG. 11 illustrates a method 410 according to an embodiment of the invention.

Method 410 of FIG. 11 differs from method 400 of FIG. 10 by:
a. Including stage 412 of receiving scattered light optics based overlay measurements;
b. Having stage 414 instead of stage 408; and
c. Not including stage 409.

Stage 414 is preceded by stages 406 and 412.

Stage 414 includes determining at least one spatial relationship between at least one feature of the first area and at least one feature of the second area based on the detection signals and on the scattered light optics based overlay measurements. The scattered light optics based overlay measurements can be referred to as first layer information. It is noted that if obtained before the first layer is manufactured on top of the second layer—then the scattered light optics based overlay measurements can represent the second area.

According to an embodiment of the invention, the overlay errors are measured as deviations from a required spatial relationship between the first and second features.

Any combination of any stages of any of the mentioned above methods can be provided. Any method can be executed by any of the systems.

The first and second areas can have any desired shape, size or location. These parameters (shape, size, location) may be determined by a user, may be set in response to previous inspection or metrology attempts, may be defined by setting a scanning pattern, and the like. The method and systems can scan one area after the other by using mechanical and, additionally or alternatively, electrical scanning and deflection processes.

The methods mentioned above or at least the computer-implemented stage of the methods mentioned above can be executed by a computer that executes code stored in a non-transitory computer readable medium. For example, the non-transitory computer readable medium can store instructions for: receiving first area information representative of a first area of a first layer of an inspected object; wherein the inspected object further comprises a second layer that comprises a second area; wherein the second layer is buried under the first layer; receiving detection signals responsive to electrons that were scattered or reflected from the first area and from a second area of a second layer that is buried under the first layer; and determining at least one spatial relationship between at least one feature of the first area and at least one feature of the second area based on the detection signals and on the first area information.

The present invention can be practiced by employing conventional tools, methodology and components. Accordingly, the details of such tools, components and methodology are not set forth herein in detail. In the previous descriptions, numerous specific details are set forth, such as shapes of cross sections of typical lines, number of deflection units, etc., in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

For example, although the mentioned above text refers to measurement of overlay errors the mentioned above method and systems can be applied mutatis mutandis to other measurements and to defect detection of buried defects.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for evaluating overlay between a first three dimensional feature formed in a first layer of an inspected object by a first lithographic process and a second feature three dimensional formed in a second layer of the inspected object buried under the first layer and formed by a second lithographic process prior to the first lithographic process, the method comprising:
obtaining or receiving first area information representative of a characteristic of the first feature formed in the first layer;
performing a multi-step imaging sequence to generate an image of at least a portion of the first and second features, the multi-step imaging sequence including: (i) directing electrons of a primary electron beam to interact with the first feature during a first imaging step; and (ii)

directing electrons of the primary electron beam to interact with the second feature during a second imaging step;

generating detection signals responsive to electrons that were scattered or reflected from each of the first and second features; and determining at least one spatial relationship in the X or Y dimensions between at least one edge of the first feature and at least one edge of the second feature based on the detection signals and on the first area information representative of the characteristic of the first feature formed in the first layer to enable differentiation between overlay errors that otherwise cannot be distinguished based on edge detection.

2. The method according to claim 1, wherein the first imaging step comprises directing electrons of the primary electron beam to interact with the first feature by selecting a landing energy for the primary electron beam that focuses the electron beam in the first layer; and wherein the method further comprises generating detection signals responsive to electrons that were scattered or reflected from the first feature.

3. The method according to claim 2, further comprising generating detection signals that are responsive to secondary electrons that were scattered or reflected from the first feature while ignoring backscattered electrons that were scattered from the inspected object.

4. The method according to claim 1, wherein the second imaging step comprises directing the primary electron beam towards the inspected object so that the electrons of the primary electron beam have a landing energy of at least 2000 electron volts.

5. The method according to claim 1, wherein the second imaging step comprises directing the primary electron beam towards the inspected object so that the electrons of the primary electron beam have a landing energy of at least 5000 electron volts.

6. The method according to claim 1 wherein the first imaging step preceeds the second imaging step.

7. The method according to claim 1, wherein
the first and second features are part of a double patterning process to increase the density of circuit features that can be produced on the inspected object beyond a normal lithography limit and wherein an expected distance between a edge of the first feature formed in the first layer and a closest edge of the second feature formed in the second layer is smaller than a pitch between adjacent features of the first layer.

8. The method according to claim 1, further comprising generating a first area detection signal responsive to secondary electrons that were scattered or reflected from the first area feature; and generating a second area detection signal responsive to backscattered electrons that were scattered or reflected from the second feature.

9. The method according to claim 7, further comprising directing the primary electron beam towards the inspected object so that the electrons of the primary electron beam have a landing energy of at least 2000 electron volts.

10. The method according to claim 7, further comprising directing the primary electron beam towards the inspected object so that the electrons of the primary electron beam have a landing energy of at least 5000 electron volts.

11. The method according to claim 7, further comprising directing the primary electron beam towards the inspected object so that the electrons of the primary electron beam have a landing energy that ranges between 2000 and 5000 electron volts.

12. A system, comprising:
a processor arranged to obtain or receive first area information representative of a characteristic of a first feature formed in a first layer of an inspected object that further includes a second feature formed in a second layer buried under the first layer;

electron optics arranged to direct electrons of a primary electron beam to interact with the inspected object;

the processor configured to perform a multi-step imaging sequence to generate an image of at least a portion of the first and second features, the multi-step imaging sequence including: (i) directing electrons of the primary electron beam to interact with the first feature during a first imaging step and (ii) directing electrons of the primary electron beam to interact with the second feature during a second imaging step; and at least one detector arranged to generate detection signals responsive to electrons that were scattered or reflected from each of the first and second features, wherein the processor is further arranged to determine at least one spatial relationship in the X or Y dimensions between at least one edge of the first feature and at least one edge of the second feature based on the detection signals and on the first area information representative of the characteristic of the first area of the first layer to enable differentiation between overlay errors that otherwise cannot be distinguished based on edge detection.

13. The system according to claim 12 wherein the first imaging step comprises directing electrons of the primary electron beam to interact with the first feature by selecting a landing energy for the primary electron beam that focuses the electron beam in the first layer; and wherein the method further comprises generating detection signals responsive to electrons that were scattered or reflected from the first feature.

14. The system according to claim 13 further comprising generating detection signals that are responsive to secondary electrons that were scattered or reflected from the first feature while ignoring backscattered electrons that were scattered from the inspected object.

15. The system according to claim 12 wherein the second imaging step comprises directing the primary electron beam towards the inspected object so that the electrons of the primary electron beam have a landing energy of at least 2000 electron volts.

16. The system according to claim 12 wherein the first imaging step preceeds the second imaging step.

17. The system according to claim 12 wherein the first and second features are part of a double patterning process to increase the density of circuit features that can be produced on the inspected object beyond a normal lithography limit and wherein an expected distance between a edge of the first feature formed in the first layer and a closest edge of the second feature formed in the second layer is smaller than a pitch between adjacent features of the first layer.

18. The method according to claim 1 wherein the second imaging step occurs at a different time than the first imaging step.

19. The system according to claim 12 wherein the second imaging step occurs at a different time than the first imaging step.

* * * * *